US007272433B2

(12) United States Patent
Riff et al.

(10) Patent No.: US 7,272,433 B2
(45) Date of Patent: Sep. 18, 2007

(54) TRANSCUTANEOUS MONITOR AND METHOD OF USE, USING THERAPEUTIC OUTPUT FROM AN IMPLANTED MEDICAL DEVICE

(75) Inventors: Kenneth M. Riff, Orono, MN (US); Gregory J. Linden, Shorewood, MN (US); James E. Willenbring, St. Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 364 days.

(21) Appl. No.: 10/136,785

(22) Filed: Apr. 30, 2002

(65) Prior Publication Data

US 2003/0004554 A1 Jan. 2, 2003

Related U.S. Application Data

(60) Provisional application No. 60/287,521, filed on Apr. 30, 2001.

(51) Int. Cl.
*A61B 5/02* (2006.01)
*A61N 1/18* (2006.01)

(52) U.S. Cl. ........................................ 600/510; 607/62
(58) Field of Classification Search .................. 607/72, 607/4–32, 62; 600/510
See application file for complete search history.

(56) References Cited

U.S. PATENT DOCUMENTS

| | | | |
|---|---|---|---|
| 4,291,703 A | | 9/1981 | Kelen |
| 4,561,443 A | | 12/1985 | Hogrefe et al. |
| 4,693,253 A | * | 9/1987 | Adams ........................... 607/4 |
| 4,958,632 A | | 9/1990 | Duggan |
| 4,987,897 A | | 1/1991 | Funke |
| 5,113,869 A | | 5/1992 | Nappholz et al. |
| 5,135,480 A | | 8/1992 | Bannon et al. |
| 5,304,209 A | | 4/1994 | Adams et al. |
| 5,309,920 A | * | 5/1994 | Gallant et al. .............. 600/523 |
| 5,443,065 A | | 8/1995 | Berghoff et al. |
| 5,445,607 A | | 8/1995 | Venkateshwaran et al. |
| 5,476,503 A | | 12/1995 | Yang |
| 5,501,230 A | * | 3/1996 | Laribiere .................... 600/508 |
| 5,558,640 A | | 9/1996 | Pfeiler et al. |
| 5,607,385 A | * | 3/1997 | Francischelli et al. ........ 600/17 |
| 5,620,473 A | * | 4/1997 | Poore .......................... 607/27 |
| 5,634,468 A | * | 6/1997 | Platt et al. .................. 600/509 |
| 5,658,247 A | | 8/1997 | Henley |
| 5,682,902 A | | 11/1997 | Herleikson |
| 5,704,351 A | | 1/1998 | Mortara et al. |
| 5,720,771 A | * | 2/1998 | Snell .......................... 607/60 |
| 5,752,976 A | | 5/1998 | Duffin et al. |

(Continued)

FOREIGN PATENT DOCUMENTS

DE  2757983 A1  6/1979

(Continued)

*Primary Examiner*—Scott M. Getzow
(74) *Attorney, Agent, or Firm*—IPLM Group, P.A.

(57) ABSTRACT

An external physiologic or implanted device monitor/controller ("monitor") designed to be attached to the body, as for example, to the skin of the patient. The monitor is designed to detect the therapeutic outputs actually produced by the implanted medical device. Having knowledge of the operation of the implanted medical device, the monitor may then deduce, or decode, the physiologic conditions and/or devices conditions sensed by the implanted medical device. The monitor is then able to perform an action appropriate to the sensed condition and the specific implementation.

62 Claims, 3 Drawing Sheets

U.S. PATENT DOCUMENTS

| | | |
|---|---|---|
| 5,759,199 A | 6/1998 | Snell et al. |
| 5,893,881 A | 4/1999 | Elsberry et al. |
| 5,925,021 A | 7/1999 | Catellano et al. |
| 5,935,078 A | 8/1999 | Feierbach |
| 5,974,341 A | 10/1999 | Er et al. |
| 6,076,016 A | 6/2000 | Feierbach |
| 6,157,858 A | 12/2000 | Gross et al. |
| 6,200,265 B1 | 3/2001 | Walsh et al. |

FOREIGN PATENT DOCUMENTS

| | | |
|---|---|---|
| EP | 0457524 A1 | 11/1991 |
| EP | 1022035 A1 | 7/2000 |
| WO | WO 00/47109 A1 | 8/2000 |

* cited by examiner

TRANSCUTANEOUS MONITOR AND METHOD OF USE, USING THERAPEUTIC OUTPUT FROM AN IMPLANTED MEDICAL DEVICE

RELATED APPLICATIONS

The present application claims priority from U.S. Provisional Patent Application Ser. No. 60/287,521, filed Apr. 30, 2001.

The present application is related to the following co-pending United States Patent Application entitled "Implantable Medical Device and Patch System and Method of Use," La Porte et al, filed on even date herewith 60/287,521, which is not admitted as prior art with respect to the present disclosure by its mention in this section.

TECHNICAL FIELD OF THE INVENTION

The present invention relates generally to medical devices and, more particularly, to a transcutaneous physiologic monitor or controller and method using therapeutic outputs from an implanted medical device.

BACKGROUND OF THE INVENTION

Implanted medical devices, such as pacemakers and implantable cardioverter defibrillators ("ICDs"), produce life-saving therapeutic outputs for the heart. Such devices, either preferably or, in the case of an ICD, necessarily, sense physiologic conditions of the body in order to adjust their operation for the benefit of the patient. Both such devices sense electrical activity native in the body in the atria and the ventricles. Such devices may also sense additional body information such as that related to activity level or respiration. Again, these devices may adjust their output in order to provide an improved benefit for the patient.

Detecting such physiologic conditions externally to the body is also desirable, and such needs could be separate and apart from the operation of the implantable medical device. Sensing the underlying physiologic condition could detect arrhythmias, hemodynamics and other functions. Further, detecting the underlying physiologic condition could also be useful for use in conjunction with the device, as, for example, detecting device malfunction.

While implanted medical devices, such as pacemakers and ICDs, are often programmed to operate automatically in response to their sensed physiologic conditions, it is difficult to monitor these devices and determine, from a location external to the patient, such underlying physiologic conditions. For example, naturally occurring electrical signals in the atria and ventricles are normally have an amplitude in the range of several millivolts. However, such signals detected at the skin surface are ordinarily in the range of millivolts to microvolts. While the implanted medical device can easily detect such native signals in the millivolt range, it is more difficult and cumbersome to detect the same signals at the skin surface.

Prior art implanted medical devices have communicated information about their operation external of the body by utilizing radio telemetry, typically in the 175 kiloHertz range. Such technique is widely used to externally interrogate the memory contained in such an implanted medical device. This technique requires a relatively sophisticated instrument such as a programmer which is capable of interacting with the implanted medical device along with computational capabilities in the instrument to decode the data in the telemetry stream.

Another prior art technique used to communicate information about the implanted medical device externally from the body is a "patient alert" type feature. In this technique, the implanted medical device may emit an audible tone intended to alert the patient if certain physiologic or medical device conditions are sensed, such as a lead problem or a low battery. However, this technique requires that the patient listen for generated audible tone, determine what the audible means and, then, contact a health care worker.

SUMMARY OF THE INVENTION

According to an embodiment of the present invention, an external physiologic or implanted device monitor/controller ("monitor") is designed to be attached to the body, as for example, to the skin of the patient. The monitor is designed to detect the therapeutic outputs actually produced by the implanted medical device. Having knowledge of the operation of the implanted medical device, the monitor may then deduce, or decode, the physiologic conditions and/or device conditions sensed by the implanted medical device. The monitor is then able to perform an action appropriate to the sensed condition and the specific implementation.

The electrical output signals of an implanted pacemaker can typically be in the range of several volts. Such signals can be readily sensed by relatively unsophisticated equipment at the skin of the patient at amplitudes in the millivolt range. Electrical signals in the millivolt range are much easier to detect at the skin surface than signals in the microvolt range. Further, the electrical output signals of an implanted ICD can typically be in the range of several hundreds of volts. Such signals can appear at the skin surface at an amplitude typically in the several volt range. Again, signals in the several volt range are much easier to detect than the signals of the underlying physiologic condition having a skin surface amplitude in the microvolt range.

Thus, an embodiment of the present invention allows an external monitor to receive physiologic data without using telemetry simply by monitoring the easily-detected therapeutic outputs, such as electrical therapy signals (e.g., pacing or high voltage cardioversion defibrillation) delivered by the implanted device. Further, there may be no need to construct the implanted medical device to generate a special signal, such as the audible "patient alert" tone to signal device malfunction, since device malfunction may often be inferred by the therapeutic outputs generated by the implanted medical device.

One embodiment of the present invention is a monitoring system for monitoring a patient. An implantable medical device is configured to be implanted into the patient. The implantable medical device is capable, when implanted, of generating a therapeutic effect to the patient according to known parameters in response to a physiologic condition of the patient. Further, the implantable medical device having an output indicative of the therapeutic effect. A monitor, externally attachable to the patient, contains a sensor for monitoring the output, deduces an underlying condition from the output and acts in response to thereto.

In another embodiment, the present invention is a monitoring device for monitoring a patient having an implanted medical device configured to generate a therapeutic effect to the patient according to known parameters in response to the physiologic condition of the patient. The implanted medical device has an output indicative of the therapeutic effect. A monitor, externally attachable to the patient, has a sensor for monitoring the output, deduces an underlying condition from the output and acts in response thereto.

In another embodiment, the present invention is a physiologic monitoring device for monitoring a physiologic condition of a patient having an implanted medical device configured to generate a therapeutic stimulus to the patient according to known parameters in response to the physiologic condition of the patient. A monitor, externally attachable to the patient, has a sensor for monitoring the therapeutic stimulus, deduces the physiologic condition from the therapeutic stimulus and acts in response thereto.

In another embodiment, the present invention is physiologic monitor, externally attachable to a patient having skin, for monitoring a physiologic condition of the patient having an implanted medical device configured to generate a therapeutic stimulus to the patient according to known parameters in response to the physiologic condition of the patient. A skin patch electrode is attached to the skin of the patient for sensing the therapeutic stimulus. An algorithm decoder, operatively coupled to the skin patch electrode, deduces the physiologic condition from the therapeutic stimulus. A signaling device, operatively coupled to the algorithm decoder, communicates the physiologic condition externally from the physiologic monitor.

In another embodiment, the present invention is a method of monitoring a patient. A medical device is implanted into the patient, the implantable medical device being capable, when implanted, of generating a therapeutic effect to the patient according to known parameters in response to the physiologic condition of the patient. The implantable medical device has an output indicative of the therapeutic effect. A monitor is externally attached to the patient, the monitor containing a sensor for monitoring the output, deducing an underlying condition from the output and acting in response thereto.

In another embodiment, the present invention is a method of monitoring a physiologic condition of a patient having an implanted medical device configured to generate a therapeutic effect to the patient according to known parameters in response to the physiologic condition of the patient. The implanted medical device has an output indicative of the therapeutic effect. The method senses the output, deduces the physiologic condition from the output and acts in response thereto.

In an embodiment, the output is a therapeutic stimulus, preferably an electrical signal.

In an embodiment, the monitor is attachable to the patient with a skin patch electrode, preferably through the use of an adhesive.

In an embodiment, the monitor acts in response thereto by communicating the underlying condition externally from the monitor using a signaling device, such as by radio-telemetry or visual indication.

In an embodiment, the monitor acts in response thereto by controlling a secondary medical device.

In an embodiment, the underlying condition is indicative of the physiologic condition.

In an embodiment, the underlying condition is of a condition of the implantable medical device.

In an embodiment, the output is a magnetic signal.

In an embodiment, the output is an acoustic signal.

In an embodiment, the monitor acts in response thereto by communicating the underlying condition externally from the monitor using a signaling device.

In an embodiment, the monitor communicates via a visual indication.

In an embodiment, the monitor acts in response thereto by controlling a secondary medical device.

In an embodiment, the underlying condition is indicative of the physiologic condition.

In an embodiment, the underlying condition is of a condition of the implantable medical device.

BRIEF DESCRIPTION OF THE DRAWINGS

Advantages and attainments, together with a more complete understanding of the present invention, will become more readily apparent and appreciated by reference to the following detailed description and claims taken in conjunction with the accompanying drawings in which:

Figure 1:
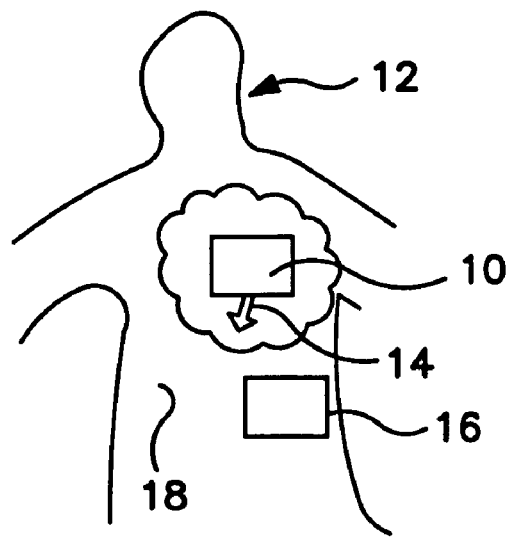
FIG. 1 is a pictorial illustration of an implantable medical device implanted in a patient in conjunction with an external monitor according to an embodiment of the present invention.

While the present invention is amenable to various modifications and alternative forms, specifics thereof have been shown by way of example in the drawings and will be described in detail hereinbelow. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF THE PREFERRED EMBODIMENTS

Examples of implantable medical devices are cardiac arrhythmia products, including pacemakers and implantable cardioverter defibrillators ("ICDs"), neurostimulators and drug pumps.

Typically such devices are either programmed to perform a therapeutic function and/or, in full or in part, sense certain physiologic conditions of the patient and/or certain conditions of the device itself and/or of its operation. The output of the implantable medical device, in part, may depend upon the sensed physiologic or device conditions. The particular output of the implantable medical device is typically predetermined, or otherwise known from the device specifications, by programming the device, before or after implantation, by the operational characteristics of the device itself and by the sensed physiologic conditions of the patient. It is frequently possible to create a one-to-one mapping between a specific type of therapeutic output and the sensed conditions that leads to that output, based on the characteristics of the specific implanted device and the way it is programmed. Thus, if one can sense the therapeutic output of a known implantable medical device, one can frequently determine the conditions sensed by that implantable medical device. Examples of this determination are provided below.

While embodiments of the present invention are useful with a variety of implantable medical devices, with a variety of therapeutic outputs, with a variety of sensed conditions, including physiologic and devices conditions, the following examples are provided using pacemakers and ICDs as the implantable medical device having an electrical output stimulus.

The therapeutic electrical output stimulus of a therapeutic implantable medical device like a pacemaker or an implantable cardioverter defibrillator ("ICD") is easily detectable from near the skin surface of the patient using electrocardiogram ("ECG") electrodes and a standard ECG preamplifier which are well known in the art. The therapeutic electrical output from a pacemaker typically consists of pacing pulses in the one to five volt range, which can be detected by skin electrodes as several millivolt signals. The high voltage defibrillation output from an ICD typically consists of ramp waveforms in the hundreds of volts range, which again can be easily detected as several volt signals on or near the skin surface.

The therapeutic electrical output of a therapeutic implantable device occurs as a response to a set of sensed conditions. The manner in which it is frequently possible to create a one-to-one mapping between a specific type of therapeutic electrical output and the sensed conditions that leads to that output, based on the characteristics of the specific implanted device and the way it is programmed, can be illustrated by way of example.

As an example, ventricular pacing in a VVI pacemaker occurs when no intrinsic ventricular electrical signal is detected by the pacemaker during a pre-set time interval. Therefore, detecting a regular set of ventricular pacing stimuli can be taken as evidence that there are no intrinsic ventricular depolarizations occurring, without having to measure intrinsic ventricular activity independently.

By way of further example, implantable therapeutic devices have evolved considerably in complexity from VVI pacing, and there are now specific therapeutic algorithms built into most devices which occur in response to a particular set of sensed condition. For example, "Rate Drop Response" is a particular type of pacing which is easily recognized by a rapid start of regular pacing at a relatively high rate (such as 120 beats per minute), followed by a gradual fallback in pacing rate over the next several minutes. This particular output is activated by a specific set of trigger criteria, including a fall in the intrinsic ventricular rate through a specific rate window over a specific time window. Therefore, the specific therapeutic output "signature" generated by the pacemaker in response to the "Rate Drop Response" condition, which is easily detectable at the skin surface, allows an external device to determine that a specific type of intrinsic rate change occurred.

Similarly, an ICD may be programmed to deliver a burst of autodecremental anti-tachycardia pacing ("ATP") if a ventricular arrhythmia of a certain rate is detected. The external monitor can easily detect the specific pattern of autodecremental ATP as an output "signature" of a ventricular arrhythmia and, similarly, identify this arrhythmia.

There are, of course, many other examples of unique therapeutic output "signatures" which can be used by the external monitoring system to generate a specific diagnosis.

In addition to detecting physiologic conditions such as arrhythmias, potential malfunctions or problems with the implanted medical device can also be detected.

For example, ventricular safety pacing occurs in response to a sensed beat during pacemaker refractory period. The safety pace is easily recognizable by its characteristic coupling interval from the previous pace. Frequent ventricular safety pacing sometimes indicates a lead insulation problem. There, the detection of frequent ventricular safety pacing could lead to the diagnosis of an underlying possible ventricular lead problem.

It may also be possible to use the diagnostic information gleaned from the therapeutic output of an implantable medical device along with directly detected intrinsic electrical activity of the heart, e.g., easily detected ORS complexes, and the known relationships between the therapeutic output of the implanted medical device and the detected intrinsic rhythm to add additional detection capability. For example, a dissociation between ventricular pacing spikes and intrinsic ventricular beats could indicate loss of capture.

An implanted device may respond with a specific therapeutic electrical intervention, based on sensed information. For example, an implantable pacemaker may be programmed to undergo a certain type of pacing rate fallback if ischemia is detected. This specific behavior of the implanted medical device, for example, could be sensed and deduced as indicative of sensed ischemia.

Figure 2:
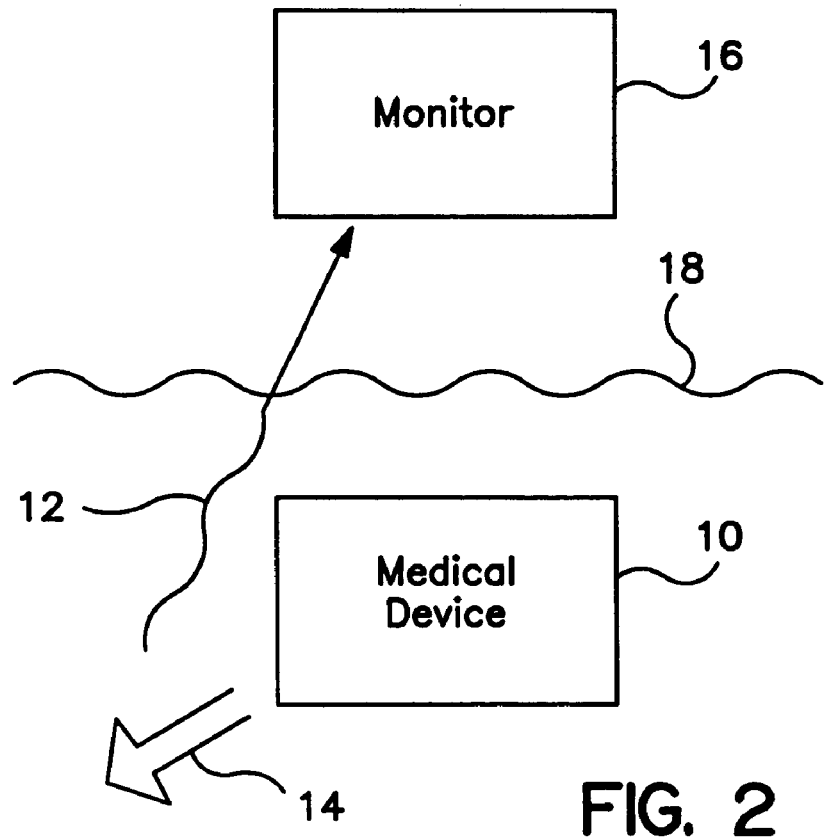
FIG. 2 is a cross-sectional schematic representation of the system of FIG. 1 illustrating its transcutaneous arrangement.

FIGS. 1 and 2 illustrate an implantable medical device 10 implanted in a patient 12. Non-limiting examples of an implantable medical device 10 are a pacemaker, an ICD, a neurostimulator or a drug pump.

An example of a pacemaker which could be utilized as part of an embodiment of the present invention may be had by reference to U.S. Pat. No. 5,271,395, Wahlstrand et al, Method and Apparatus For Rate-Responsive Cardiac Pacing, the contents of which is hereby incorporated by reference.

An example of an ICD which could be utilized as part of an embodiment of the present invention may be had by reference to U.S. Pat. No. 5,163,427, Keimel, Apparatus For Delivering Single and Multiple Cardioversion and Defibrillation Pulses, the contents of which is hereby incorporated by reference.

An example of a neurostimulator which could be utilized as part of an embodiment of the present invention may be had by reference to a Synergy™ implantable neurostimulator[1], manufactured and sold by Medtronic, Inc., Fridley, Minn.

[1]Synergy is a trademark of Medtronic, Inc., Fridley, Minn.

An example of an implantable drug pump which could be utilized as part of an embodiment of the present invention may be had by reference to a Synchromed® II implantable programmable pump[2], manufactured and sold by Medtronic, Inc., Fridley, Minn.

[2]Synchromed is a trademark of Medtronic, Inc., Fridley, Minn.

Implantable medical device 10 provides an output 14 as part of rendering a therapeutic effect to patient 12. In some embodiments of the present invention, output 14 may be an intended stimulus provided to patient 12 by implantable medical device 10. Non-limiting examples of intended stimuli would include electrical signals such as electrical pacing signals supplied by a pacemaker, electrical defibrillation ("shock") signals provided by an ICD and electrical signals supplied by a neurostimulator. In another embodiments of the present invention, output 14 may be incidental to the providing of therapeutic effect to patient 12 by implantable medical device 10. Non-limiting examples of incidental output would be "ringing" in output circuits, acoustic sounds generated by capacitors charging or discharging, and acoustic sounds generated by pumps, e.g., as in a drug pump dispensing medication.

Monitor 16 is illustrated in FIG. 1 externally attached adjacent to or relatively near to the skin 18 of patient 12. It is preferred that monitor 16 be attached in a position on the body of patient 12 in relatively close proximity to the output 14 intended to be monitored by monitor 16.

Monitor 16 may detect the output of implantable medical device 10 transcutaneously while the implantable medical device 10 renders a therapeutic effect to patient 12. In some embodiments of the present invention, monitor 16 may detect an electrical field produced by implantable medical device 10. Non-limiting examples of situations in which an electrical field detection technique may be appropriate are high energy discharges ("shock") from an ICD, low energy discharges ("pacing") from a pacemaker, and "ringing" in circuits, especially output circuits, of electrical stimulators, including pacemakers, ICDs and neurostimulators. In other embodiments of the present invention, monitor 16 may detect a magnetic field produced by implantable medical device 10. Non-limiting examples of situations in which a magnetic field detection technique may be appropriate are high energy discharges ("shock") from an ICD, low energy discharges ("pacing") from a pacemaker, and "ringing" in circuits, especially output circuits, of electrical stimulators, including pacemakers, ICDs and neurostimulators. In other embodiments of the present invention, monitor 16 may detect an acoustic sound produced by implanted medical device 10, e.g., acoustic sounds produced incidental in the performance of producing a therapeutic effect on patient 12. Non-limiting examples of situations in which an acoustic detection technique may be appropriate include sounds produced by capacitors charging or discharging in an ICD and pump sounds made by an implantable drug pump.

Monitor 16, upon detection of a physiologic or device condition (as described above), then acts upon such detection, decoding or deducement.

Figure 3:
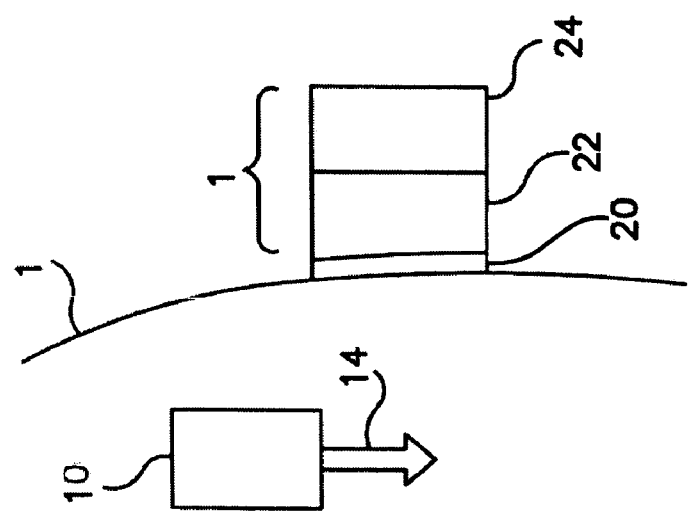
FIG. 3 is an illustration of an embodiment of the present invention utilizing external signaling.

In some embodiments of the present invention, monitor 16 acts upon such detection by communicating such detection external to monitor 16. In this way, monitor 16 acts as a true monitor and communicates the results of its monitoring to someone or something else. FIG. 3 illustrates these embodiments. Monitor 16 is attached to skin 18 of patient 12 with skin patch electrode 20. Electrode 20 senses the output of implantable medical device 10 and sends a signal to algorithm decoder 22 of monitor 16. Algorithm decoder 22 determines if one of the predetermined sensed conditions are present and communicates such detection externally via signaling device 24.

Signaling device 24 may any one or more of any number of known ways to signal. In some embodiments of the present invention, signaling device 24 may use well known radio-frequency telemetry, possibly including messaging, to communicate to or with an external receiver. In other embodiments of the present invention, signaling device 24 may use a visual indicator or visual indication, such as a light, a change in color, a change in intensity of light, or an alpha, numeric or an alpha-numeric display. In other embodiments of the present invention, signaling device 24 may use a vibration, possibly including different speeds, rates or characteristics of vibration, or other form of tactile sensation. In other embodiments of the present invention, signaling device 24 may use a change in temperature as an indicator. In other embodiments of the present invention, signaling device 24 may use an acoustic signal, possibly including speech. In short, the range of ways to communicate are many.

Figure 4:
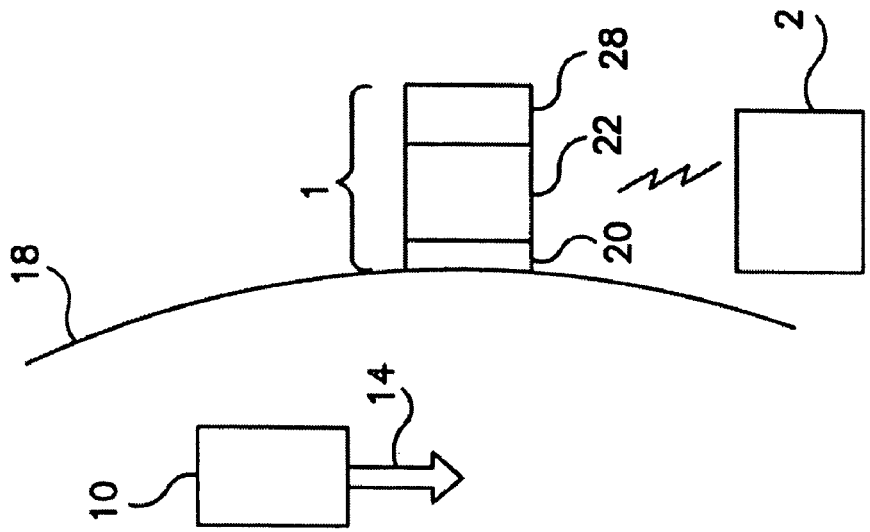
FIG. 4 is an illustration of an embodiment of the present invention utilizing control over a second medical device.

In other embodiments of the present invention (illustrated in FIG. 4), monitor 16, while being called a monitor, acts as a controller to control another device, such as another medical device 26. Such control function may be instead of the communication described with reference to FIG. 3 or may be in addition to such communication.

Similar to FIG. 3, monitor 16 is attached to skin 18 of patient 12 with skin patch electrode 20. Electrode 20 senses the output of implantable medical device 10 and sends a signal to algorithm decoder 22 of monitor 16. Algorithm decoder 22 determines if one of the predetermined sensed conditions are present. Perhaps instead of, or perhaps in addition to communicating such detection externally via signaling device 24, monitor 16 controls a second medical device 26 via control module 28. Medical device 26 may be implanted or may be external to the body patient 12. Further, medical device 26 may be located in the proximity of monitor 16, or attached to monitor 16, or may be located relatively distant to monitor 16.

Since monitor 16 may be able to determine underlying physiologic conditions of patient 12 or underlying conditions of implantable medical device 10, monitor 16 may be able to control second medical device 26 in accordance with those underlying physiologic conditions or underlying device conditions. Thus, a second medical device 26 may be able to render therapeutic effect on patient 12 responsive to physiologic conditions of patient 12, or responsive to device conditions of implantable medical device 10, without incurring the cost, complexity or difficulty of directly sensing such underlying conditions.

In one preferred embodiment, implantable medical device 10 is a pacemaker which can provide therapeutic electrical signals to patient 12 based upon sensed physiologic conditions of patient 12. Second medical device 26 is an external drug infusion patch which may be attached to the skin of patient 26. External drug infusion patch is able to be controlled to administer medication to patient 12 based upon underlying physiologic conditions of patient 12. For example, if the internal pacemaker or defibrillator (implantable medical device 10) detects atrial tachycardia and administers a particular stimulus such as anti-tachycardia pacing, monitor 16 detects that underlying condition and alerts external drug infusion patch (second medical device 26). In this case, external drug infusion patch may administer medication appropriate for the circumstance, such as delivering an antiarrhythmic drug.

This arrangement is described in more detail in the following co-pending United States Patent Application entitled "Implantable Medical Device and Patch System and Method of Use," La Porte et al, filed on even date herewith 60/287,521, which is hereby incorporated by reference. The arrangement described in this patent application utilized radio frequency telemetry to communicate the status of implantable medical device for use by an external drug infusion patch, known as a "smart drug infusion patch." While the present invention does not contemplate communication between implantable medical device 10 and monitor 16 via radio frequency telemetry, the same techniques described in this application for controlling a second medical device apply equally to the technique of the present invention of detecting the underlying physiologic conditions or underlying device conditions by way of sensing the therapeutic effects of implantable medical device 10 as described herein.

A pacemaker which could be utilized in connection with the present invention as implantable medical device 10 is described in the aforementioned U.S. Pat. No. 5,271,395, Wahlstrand et al.

Figure 5:
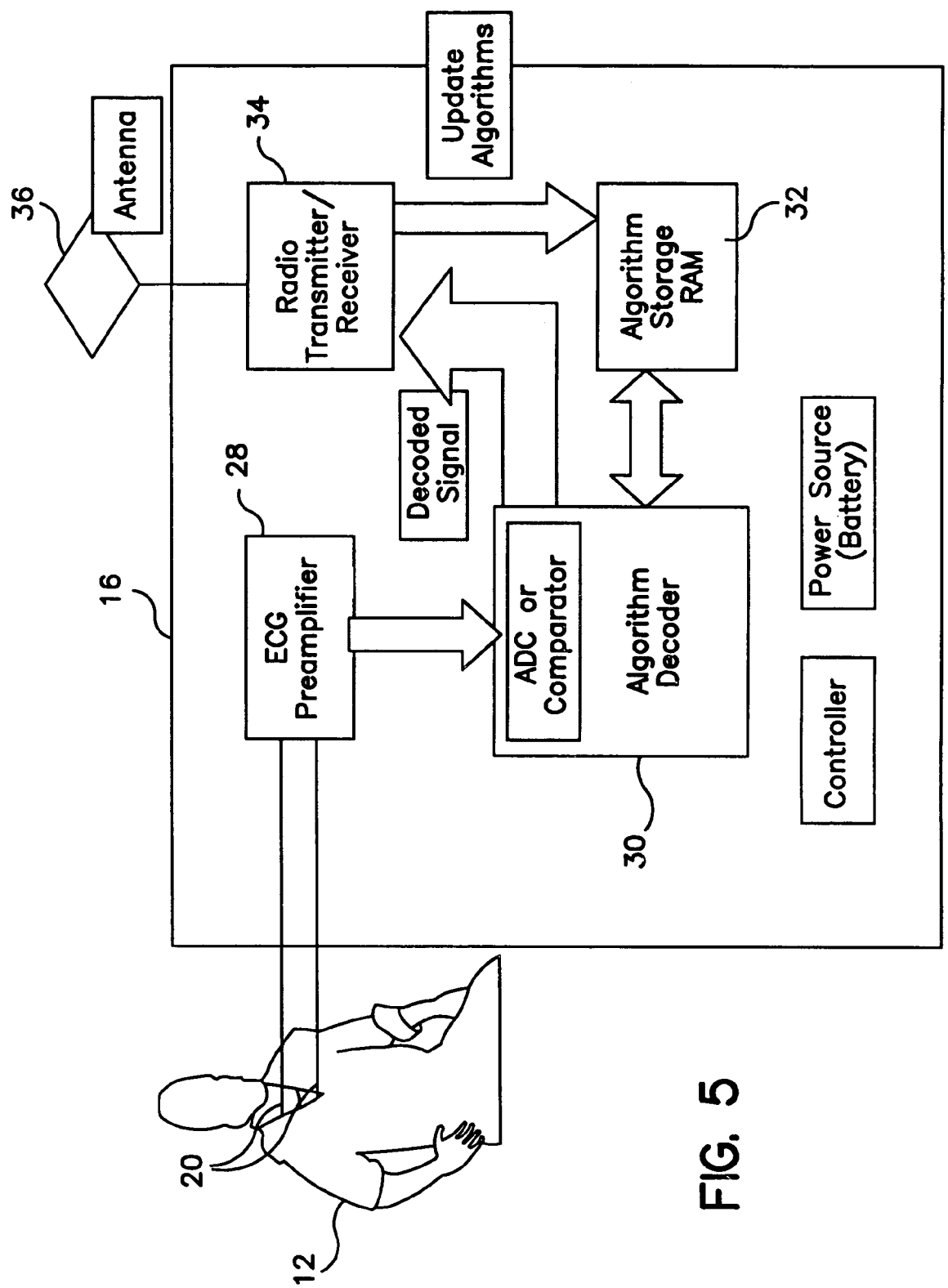
FIG. 5 is a detailed schematic representation of an embodiment of the monitor of the present invention.

Detailed construction of a preferred embodiment of monitor 16 is illustrated in FIG. 5. Electrodes 20 are applied to the patient 12 and connected to an electrocardiogram ("ECG")

preamplifier 28. ECG preamplifier 28 sends the amplified signal to algorithm decoder 30. Algorithm decoder 30 typically contains either an analog-to-digital converter ("ADC") or an analog sense amplifier with comparator circuitry in order to detect therapeutic electrical signals. The output from the ADC or comparator is then sequentially fed to the algorithm decoder circuitry which compares the incoming signal with a set of patterns stored in algorithm storage RAM 32. Algorithm storage RAM 32 contains the specific therapeutic patterns that are used to decode the therapeutic electrical signals into specific patterns. Algorithm storage RAM 32 is customizable for the specific implantable medical device 10. For example, ventricular tachycardia ("VT") at a certain rate might be programmed to cause implantable medical device 10 to initiate a specific type of ATP. This information could then be loaded into algorithm storage RAM 32. Algorithm decoder 30 compares the sensed therapeutic electrical signals as supplied by ECG preamplifier 28 with the information contained in algorithm storage RAM 32. If the comparison is successful, algorithm decoder 30 determines that sensed condition is present and monitor 16 acts accordingly. In this embodiment, the result of the comparison is sent to radio frequency transmitter/receiver 34 to communication of the condition external to monitor 16 utilizing antenna 36.

As in the example given above, autodecremental ATP in response to a detected VT might generate a "10001000" radio signal, while a defibrillation shock might generate a "11111111" radio signal, which the receiver would decode into the appropriate sensed rhythm. In the example give above, other conditions such as excess ventricular safety pacing, dissociation between pacing and intrinsic beasts, or a specific rate fallback behavior indicating ischemia would also generate unique identifying codes.

In a preferred embodiment of the present invention, FIG. 5 also illustrates how radio transmitter/receiver 34 can also function as a receiver to program algorithm storage RAM 32. Algorithm storage RAM 32 could also contain a programmable logic array ("PLA") that translates each detected therapeutic electrical pattern into a simple signal that is then sent to the radio transmitter/receiver 34 for transmission to the receiving system.

The preceding specific embodiments are illustrative of the practice of the invention. It is to be understood, therefore, that other expedients known to those skilled in the art or disclosed herein may be employed without departing from the invention or the scope of the following claims.

What is claimed is:

1. A monitoring system for monitoring a patient, comprising:
    an implantable medical device configurable to be implanted into said patient, said implantable medical device being capable, when implanted, of generating a therapeutic effect to said patient according to known parameters in response to a physiologic condition of said patient, said implantable medical device having a therapeutic output; and
    a monitor, externally attachable to said patient, containing a sensor for monitoring said therapeutic output, deducing an underlying condition from said therapeutic output and acting in response thereto.

2. A monitoring system as in claim 1 wherein said therapeutic output is a therapeutic stimulus.

3. A monitoring system as in claim 2 wherein said therapeutic stimulus is an electrical signal.

4. A monitoring system as in claim 3 wherein said implanted medical device is configured to generate said therapeutic stimulus to said patient according to known predetermined parameters in response to said physiologic condition.

5. A monitoring system as in claim 4 wherein said monitor is attachable to said patient with a skin patch electrode.

6. A monitoring system as in claim 5 wherein said skin parch electrode is attached to said skin of said patient through the use of an adhesive.

7. A monitoring system as in claim 1 wherein said monitor acts in response thereto by communicating said underlying condition externally from said monitor using a signaling device.

8. A monitoring system as in claim 7 wherein said signaling device utilizes radiotelemetry communication to an external receiver.

9. A monitoring system as in claim 7 wherein said monitor communicates via a visual indication.

10. A monitoring system as in claim 1 wherein said monitor acts in response thereto by controlling a secondary medical device.

11. A monitoring system as in claim 1 wherein said underlying condition is indicative of said physiologic condition.

12. A monitoring system as in claim 1 wherein said underlying condition is of a condition of said implantable medical device.

13. A monitoring device for monitoring a patient having an implanted medical device configured to generate a therapeutic effect to said patient according to known parameters in response to said physiologic condition of said patient, said implanted medical device having a therapeutic output, comprising a monitor, externally attachable to said patient, a sensor for monitoring said output, deducing an underlying condition from said therapeutic output and acting in response thereto.

14. A monitoring device as in claim 13 wherein said therapeutic output is a therapeutic stimulant.

15. A monitoring device as in claim 14 wherein said patient has skin and wherein said monitor is externally attachable to said skin of said patient.

16. A monitoring device as in claim 15 wherein said monitor is attachable to said patient with a skin patch electrode.

17. A monitoring device as in claim 16 wherein said skin patch electrode is attached to said skin of said patient though the use of an adhesive.

18. A monitoring device as in claim 14 wherein said therapeutic stimulus is an electrical signal.

19. A monitoring device as in claim 18 wherein said implanted medical device is configured to generate said electrical signal to said patient according to known predetermined parameters in response to said physiologic condition.

20. A monitoring device as in claim 13 wherein said therapeutic output is a magnetic signal.

21. A monitoring device as in claim 13 wherein said therapeutic output is an acoustic signal.

22. A monitoring device as in claim 13 wherein said monitor acts in response thereto by communicating and underlying condition externally from said monitor using a signaling device.

23. A monitoring device as in claim 22 wherein said signaling device utilizes radio-telemetry communication to an external receiver.

24. A monitoring device as in claim 22 wherein said monitor communicates via a visual indication.

25. A monitoring device as in claim 13 wherein said monitor acts in response thereto by controlling a secondary medical device.

26. A monitoring device as in claim 13 wherein said underlying condition is indicative of said physiologic condition.

27. A monitoring device as in claim 13 wherein said underlying condition is of a condition of said implantable medical device.

28. A physiologic monitoring device for monitoring a physiologic condition of a patient having an implanted medical device configured to generate a therapeutic stimulus to said patient according to known parameters in response to said physiologic condition of said patient, comprising a monitor, externally attachable to said patient, a sensor for monitoring said therapeutic stimulus, deducing said physiologic condition from said therapeutic stimulus and acting in response thereto.

29. A physiologic monitoring device as in claim 28 wherein said patient has skin and wherein said monitor is externally attachable to said skin of said patient.

30. A physiologic monitoring device as in claim 29 wherein said monitor is attachable to said patient with a skin patch electrode.

31. A physiologic monitoring device as in claim 30 wherein said skin patch electrode is attached to said skin of said patient through the use of an adhesive.

32. A physiologic monitoring device as in claim 28 wherein said therapeutic stimulus is an electrical signal.

33. A physiologic monitoring device as in claim 28 wherein said implanted medical device is configured to generate said therapeutic stimulus to said patient according to known predetermined parameters in response to said physiologic condition.

34. A physiologic monitoring device as in claim 28 wherein said monitor acts in response thereto by communicating said underlying condition externally from said monitor using a signaling device.

35. A physiologic monitoring device as in claim 34 wherein said signaling device utilizes radio-telemetry communication to an external receiver.

36. A physiologic monitoring device as in claim 34 wherein said monitor communicates via a visual indication.

37. A physiologic monitoring device as in claim 28 wherein said monitor acts in response thereto by controlling a secondary medical device.

38. A physiologic monitor, externally attachable to a patient having skin, for monitoring a physiologic condition of said patient having an implanted medical device configured to generate a therapeutic stimulus to said patient according to known parameters in response to said physiologic condition of said patient, comprising:
    a skin patch electrode attached to said skin of said patient for sensing said therapeutic stimulus;
    an algorithm decoder, operatively coupled to said skin patch electrode, for deducing said physiologic condition from said therapeutic stimulus; and
    signaling device; operatively coupled to said algorithm decoder, communicating said physiologic condition externally from said physiologic monitor.

39. A physiologic monitor as in claim 38 wherein said therapeutic stimulus is an electrical signal.

40. A physiologic monitor as in claim 38 wherein said implanted medical device is configured to generate said therapeutic stimulus to said patient according to known predetermined parameters in response to said physiologic condition.

41. A physiologic monitor as in claim 38 wherein algorithm decoder is programmable via an external programming device.

42. A physiologic monitor as in claim 38 wherein said signaling device utilizes radio-telemetry communication to an external receiver.

43. A physiologic monitor as in claim 38 wherein said signaling device comprises a visual indicator.

44. A method of monitoring a patient, comprising the steps of:
    implanting a medical device into said patient, said implantable medical device being capable, when implanted, of generating a therapeutic effect to said patient according to known parameters in response to said physiologic condition of said patient, said implantable medical device having therapeutic output; and
    externally attaching a monitor to said patient, said monitor containing a sensor for monitoring said output, deducing an underlying condition from said therapeutic output and acting in response thereto.

45. A method of monitoring as in claim 44 wherein said therapeutic output is a therapeutic stimulus.

46. A method of monitoring as in claim 45 wherein said therapeutic stimulus is an electrical signal.

47. A method of monitoring as in claim 46 wherein said implanted medical device is configured to generate said therapeutic stimulus to said patient according to known predetermined parameters in response to said physiologic condition.

48. A monitoring system as in claim 44 wherein said monitor acts in response thereto by communicating said underlying condition externally from said monitor using a signaling device.

49. A method of monitoring as in claim 48 wherein said signaling device utilizes radio-telemetry communication to an external receiver.

50. A method of monitoring as in claim 48 wherein said monitor communicates via a visual indication.

51. A method of monitoring as in claim 44 wherein said monitor acts in response thereto by controlling a secondary medical device.

52. A method of monitoring as in claim 44 wherein said underlying condition is indicative of said physiologic condition.

53. A method of monitoring as in claim 44 wherein said underlying condition is of a condition of said implantable medical device.

54. A method of monitoring a physiologic condition of a patient having an implanted medical device configured to generate a therapeutic effect to said patient according to known parameters in response to said physiologic condition of said patient, said implanted medical device having therapeutic output, comprising the steps of:
    sensing said therapeutic output;
    deducing said physiologic condition from said therapeutic output; and
    acting in response thereto.

55. A method of monitoring as in claim 54 wherein said therapeutic output is a therapeutic stimulus.

56. A method of monitoring as in claim 55 wherein said therapeutic stimulus is an electrical signal.

57. A method of monitoring as in claim 56 wherein said implanted medical device is configured to generate said therapeutic stimulus to said patient according to known predetermined parameters in response to said physiologic condition.

58. A method of monitoring as in claim 57 wherein said sensing step is accomplished via a skin patch attached to said skin of said patient.

59. A method of monitoring as in claim 54 wherein said therapeutic output is a magnetic signal.

60. A method of monitoring as in claim 54 wherein said therapeutic output is an acoustic signal.

61. A method of monitoring as in claim 54 wherein said monitor acts in response thereto by providing a visual indication.

62. A method of monitoring as in claim 54 wherein said monitor acts in response thereto by controlling a secondary medical device.

* * * * *

UNITED STATES PATENT AND TRADEMARK OFFICE
CERTIFICATE OF CORRECTION

PATENT NO. : 7,272,433 B2  Page 1 of 1
APPLICATION NO. : 10/136785
DATED : September 18, 2007
INVENTOR(S) : Riff et al.

It is certified that error appears in the above-identified patent and that said Letters Patent is hereby corrected as shown below:

Col. 10, Line 37: "therapeutic stimulant." should read --therapeutic stimulus--.

Signed and Sealed this

Twenty-ninth Day of April, 2008

JON W. DUDAS
*Director of the United States Patent and Trademark Office*